US008409084B2

(12) United States Patent
Battles

(10) Patent No.: US 8,409,084 B2
(45) Date of Patent: Apr. 2, 2013

(54) SURGICAL PORTAL APPARATUS INCLUDING GEAR AND LOCKOUT ASSEMBLY

(75) Inventor: Christopher A. Battles, Seymour, CT (US)

(73) Assignee: Covidien LP, Mansfield, MA (US)

( * ) Notice: Subject to any disclaimer, the term of this patent is extended or adjusted under 35 U.S.C. 154(b) by 330 days.

(21) Appl. No.: 12/846,380

(22) Filed: Jul. 29, 2010

(65) Prior Publication Data
US 2011/0054261 A1 Mar. 3, 2011

Related U.S. Application Data

(60) Provisional application No. 61/238,232, filed on Aug. 31, 2009.

(51) Int. Cl.
*A61B 1/3132* (2006.01)
(52) U.S. Cl. ..................................................... 600/204
(58) Field of Classification Search .................. 600/201, 600/202, 204, 205, 208, 210; 604/158–163, 604/164.08, 164.11, 167.01–167.05; 606/108; 16/354
See application file for complete search history.

(56) References Cited

U.S. PATENT DOCUMENTS

| | | | |
|---|---|---|---|
| 4,795,426 A | 1/1989 | Jones | |
| 4,917,668 A | 4/1990 | Haindl | |
| 4,943,280 A | 7/1990 | Lander | |
| 5,104,383 A | 4/1992 | Shichman | |
| 5,127,626 A | 7/1992 | Hilal et al. | |
| 5,127,909 A | 7/1992 | Shichman | |
| 5,180,373 A | 1/1993 | Green et al. | |
| 5,197,955 A | 3/1993 | Stephens et al. | |
| 5,209,736 A | 5/1993 | Stephens et al. | |
| 5,209,737 A * | 5/1993 | Ritchart et al. | 604/167.03 |
| 5,242,412 A | 9/1993 | Blake, III | |
| 5,304,143 A | 4/1994 | Green et al. | |
| 5,308,336 A | 5/1994 | Hart et al. | |
| 5,342,315 A | 8/1994 | Rowe et al. | |
| 5,350,364 A | 9/1994 | Stephens et al. | |
| 5,354,280 A | 10/1994 | Haber et al. | |
| 5,360,417 A | 11/1994 | Gravener et al. | |
| 5,380,288 A | 1/1995 | Hart et al. | |

(Continued)

FOREIGN PATENT DOCUMENTS

EP 1 702 575 A2 9/2006
GB 2 298 906 A 9/1996

(Continued)

OTHER PUBLICATIONS

Extended European Search Report corresponding to European Application No. 06006538.0, completed Jul. 18, 2006; dated Jul. 25, 2006; 5 pages.

*Primary Examiner* — Todd Manahan
*Assistant Examiner* — Eric S Gibson

(57) ABSTRACT

A surgical portal apparatus includes a portal, a seal, a plurality of restricting members, and a lockout assembly. The portal defines a longitudinal axis and has a longitudinal opening. The seal is disposed in mechanical cooperation with the portal and defines a passage for reception of a surgical object. The plurality of restricting members are arranged about the longitudinal axis to define a passage therethrough and positioned to contact the surgical object. The restricting members have contacting segments adapted for radial movement relative to the longitudinal axis from a rest position to a displaced position. The lockout assembly includes a locking member disposed distal of the restricting members. The locking member is positioned to intersect the longitudinal opening and engage the surgical object. The locking member is operatively coupled with the restricting members to minimize offset manipulation of the surgical object.

18 Claims, 5 Drawing Sheets

U.S. PATENT DOCUMENTS

| | | |
|---|---|---|
| 5,388,553 A | 2/1995 | Burke et al. |
| 5,389,081 A | 2/1995 | Castro |
| 5,391,153 A | 2/1995 | Haber et al. |
| 5,391,154 A | 2/1995 | Young |
| 5,397,314 A | 3/1995 | Farley et al. |
| 5,407,433 A | 4/1995 | Loomas |
| 5,411,483 A | 5/1995 | Loomas et al. |
| 5,443,452 A | 8/1995 | Hart et al. |
| 5,484,418 A | 1/1996 | Quiachon et al. |
| 5,485,553 A | 1/1996 | Kovalick et al. |
| 5,492,304 A | 2/1996 | Smith et al. |
| 5,496,280 A | 3/1996 | Vandenbroek et al. |
| 5,542,931 A | 8/1996 | Gravener et al. |
| 5,545,142 A | 8/1996 | Stepehns et al. |
| 5,549,565 A | 8/1996 | Ryan et al. |
| 5,584,850 A | 12/1996 | Hart et al. |
| 5,591,137 A | 1/1997 | Stevens |
| 5,603,702 A | 2/1997 | Smith et al. |
| 5,613,954 A | 3/1997 | Nelson et al. |
| 5,628,732 A | 5/1997 | Antoon, Jr. et al. |
| 5,634,908 A | 6/1997 | Loomas |
| 5,657,963 A | 8/1997 | Hinchliffe et al. |
| 5,685,854 A | 11/1997 | Green et al. |
| 5,693,025 A | 12/1997 | Stevens |
| 5,693,031 A | 12/1997 | Ryan et al. |
| 5,709,654 A | 1/1998 | Klatz et al. |
| 5,709,664 A | 1/1998 | Vandenbroek et al. |
| 5,720,759 A | 2/1998 | Green et al. |
| 5,722,958 A | 3/1998 | Gravener et al. |
| 5,727,770 A | 3/1998 | Dennis |
| 5,752,938 A | 5/1998 | Flatland et al. |
| 5,752,970 A | 5/1998 | Yoon |
| 5,782,812 A | 7/1998 | Hart et al. |
| 5,792,113 A | 8/1998 | Kramer et al. |
| 5,803,919 A | 9/1998 | Hart et al. |
| 5,814,026 A | 9/1998 | Yoon |
| 5,820,600 A | 10/1998 | Carlson et al. |
| 5,820,604 A | 10/1998 | Fox et al. |
| 5,827,228 A | 10/1998 | Rowe |
| 5,871,471 A | 2/1999 | Ryan et al. |
| 5,895,377 A | 4/1999 | Smith et al. |
| 5,913,847 A | 6/1999 | Yoon |
| 5,935,122 A | 8/1999 | Fourkas et al. |
| 5,941,852 A | 8/1999 | Dunlap et al. |
| 5,989,224 A | 11/1999 | Exline et al. |
| 5,989,232 A | 11/1999 | Yoon |
| 5,989,233 A | 11/1999 | Yoon |
| 6,066,117 A | 5/2000 | Fox et al. |
| 6,083,203 A | 7/2000 | Yoon |
| 6,093,176 A | 7/2000 | Dennis |
| 6,123,689 A | 9/2000 | To et al. |
| 6,197,016 B1 | 3/2001 | Fourkas et al. |
| 6,228,061 B1 | 5/2001 | Flatland et al. |
| 6,383,160 B1 | 5/2002 | Madsen |
| 6,450,992 B1 | 9/2002 | Cassidy, Jr. |
| 6,458,103 B1 | 10/2002 | Albert et al. |
| 6,482,181 B1 | 11/2002 | Racenet et al. |
| 6,514,260 B1 | 2/2003 | Zdeblick et al. |
| 6,569,120 B1 | 5/2003 | Green et al. |
| 6,702,787 B2 | 3/2004 | Racenet et al. |
| 6,834,842 B2 | 12/2004 | Houde |
| 6,981,966 B2 | 1/2006 | Green et al. |
| 7,025,747 B2 * | 4/2006 | Smith ............... 604/167.06 |
| 7,027,547 B1 | 4/2006 | Hwang |
| 7,063,685 B2 | 6/2006 | Rome |
| 7,179,263 B2 | 2/2007 | Zdeblick et al. |
| 2002/0072713 A1 | 6/2002 | Almond et al. |
| 2003/0187397 A1 | 10/2003 | Vitali |
| 2004/0064100 A1 | 4/2004 | Smith |
| 2004/0082969 A1 | 4/2004 | Kerr |
| 2004/0236347 A1 | 11/2004 | Karasawa |
| 2005/0010238 A1 | 1/2005 | Potter et al. |
| 2005/0070851 A1 | 3/2005 | Thompson et al. |
| 2005/0165281 A1 | 7/2005 | Ravikumar et al. |
| 2006/0020281 A1 | 1/2006 | Smith |
| 2006/0047284 A1 | 3/2006 | Gresham |
| 2008/0091144 A1 | 4/2008 | Moran et al. |

FOREIGN PATENT DOCUMENTS

| | | |
|---|---|---|
| WO | WO 93/01850 A1 | 2/1993 |
| WO | WO 94/07552 A1 | 4/1994 |
| WO | WO 01/52754 A1 | 7/2001 |
| WO | WO 01/89397 A1 | 11/2001 |
| WO | WO 02/30305 A2 | 4/2002 |

* cited by examiner

SURGICAL PORTAL APPARATUS INCLUDING GEAR AND LOCKOUT ASSEMBLY

CROSS REFERENCE TO RELATED APPLICATION

The present application claims the benefit of and priority to U.S. Provisional Application Ser. No. 61/238,232 filed on Aug. 31, 2009, the entire contents of which are incorporated herein by reference.

BACKGROUND

1. Technical Field

The present disclosure relates to a surgical portal apparatus adapted to permit the introduction of surgical instrumentation into a patient's body in sealing engagement therewith. In particular, the present disclosure is directed to a surgical portal apparatus including a gear and lockout assembly for substantially minimizing excessive angulation of the instrumentation within the apparatus thereby maintaining the integrity of the seal about the instrument and through the apparatus.

2. Background of Related Art

In laparoscopic procedures, surgery is performed in the interior of the abdomen through a small incision. In endoscopic procedures, surgery is performed in any hollow viscus of the body through a narrow tube or cannula inserted through a small entrance incision in the skin. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. Moreover, laparoscopic and endoscopic procedures often require the surgeon to act on organs, tissue, and vessels far removed from the incision, thereby requiring that any instruments used in such procedures be relatively long and narrow.

For such procedures, the introduction of a tube into certain anatomical cavities such as the abdominal cavity is usually accomplished by use of a trocar assembly made up of a cannula assembly and an obturator assembly. Since the cannula assembly provides a direct passage for surgical instrumentation from outside the patient's body to access internal organs and tissue, it is important that the cannula assembly maintain a relatively fluid-tight interface between the abdominal cavity and the outside atmosphere. The cannula assembly generally includes a cannula attached to a cannula housing containing a seal assembly adapted to maintain a seal across the opening of the cannula housing.

Since surgical procedures in the abdominal cavity of the body require insufflating gases to raise the cavity wall away from vital organs, the procedure is usually initiated by use of a Verres needle through which a gas such as $CO_2$ is introduced into the body cavity, thereby creating a pneumoperitoneum. The gas provides a positive pressure which raises the inner body wall away from internal organs, thereby providing the surgeon with a region within which to operate and avoiding unnecessary contact with the organs by the instruments inserted through the cannula assembly. An obturator of the obturator assembly is inserted into the cannula assembly and used to puncture the abdominal wall. Following removal of the obturator assembly from the cannula assembly, laparoscopic or endoscopic surgical instruments may be inserted through the cannula assembly to perform surgery within the abdominal cavity.

Generally in the context of insufflatory surgical procedures, there are two sealing requirements for cannula assemblies. The first requirement is to provide a substantially fluid-tight seal when an instrument is not being introduced into or is not already present in the cannula. The second requirement is to provide a substantially fluid-tight seal when an instrument is being introduced into or is already present in the cannula. Additionally, as endoscopic and laparoscopic surgical procedures and techniques have advanced, it has become desirable to accommodate surgical instrumentation of varying outside diameters through a single cannula assembly in a given surgical procedure, thereby minimizing the number of cannulae required and facilitating efficiency in the surgical procedure. It is further desirable to maintain a seal about the instrument for manipulation of the instrument within the cannula assembly. Although attempts have been made to provide a seal assembly as part of or for use in conjunction with a cannula assembly which maintains the integrity of the seal between the body cavity and the atmosphere outside the patient's body, seal systems provided to date have failed to address the full range of surgeons' needs.

SUMMARY

Accordingly, a surgical portal apparatus includes a portal dimensioned for insertion within tissue to access an underlying tissue site. The portal defines a longitudinal axis and has a longitudinal opening for reception of a surgical object. At least one seal is disposed in mechanical cooperation with the portal, and defines a passage for reception of the surgical object in substantial sealed relation therewith. A plurality of restricting members is arranged about the longitudinal axis to define a passage and is positioned to contact the surgical object during introduction through the longitudinal opening. The restricting members have contacting segments adapted for radial movement relative to the longitudinal axis from a rest position where the passage defines a first internal dimension to a displaced position where the passage defines a second internal dimension greater than the first internal dimension in response to contact with the surgical object. A lockout assembly including a locking member is disposed distal of the restricting members. The locking member is positioned to intersect the longitudinal opening and engage the surgical object during passage of the surgical object through the longitudinal opening. The locking member is operatively coupled with the restricting members to substantially prevent radial movement of the contacting segments beyond the displaced position when the surgical object is within the longitudinal opening, to thereby minimize offset manipulation of the surgical object relative to the longitudinal axis. A biasing member may be incorporated for normally biasing the restricting members toward the first position to urge the surgical object to the general aligned position with the longitudinal axis.

The restricting members may be operatively coupled whereby the contacting segments of the restricting members concurrently move between the rest position and the displaced position. A gear assembly for facilitating concurrent radial movement of the contacting segments of the restricting members between the rest position and the displaced position may be provided. The gear assembly may include at least one gear operatively coupling adjacent restricting members. The restricting members may be pivotally mounted within the portal whereby the contacting segments pivot between the rest position and the displaced position.

The lockout assembly may include a rack and associated drive gear operatively coupled to one of the restricting members. The drive gear is adapted for rotational movement during radial movement of the contacting segments between the rest position and the displaced position to cause corresponding longitudinal translation of the rack within the portal. A lock out pawl may be coupled to the locking member. The lock out pawl is movable upon movement of the locking member during passage of the surgical object through the longitudinal opening to selectively engage the rack to secure the rack at a defined longitudinal position corresponding to the displaced position of the contacting segments, to thereby substantially prevent radial movement of the contacting segments beyond the displaced position. The locking member is adapted for pivotal movement upon engagement with the surgical object to move the lock out pawl into engagement with the rack. The locking member may be normally biased to a position permitting release of the lock out pawl from the rack.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF EMBODIMENTS

Figure 1:
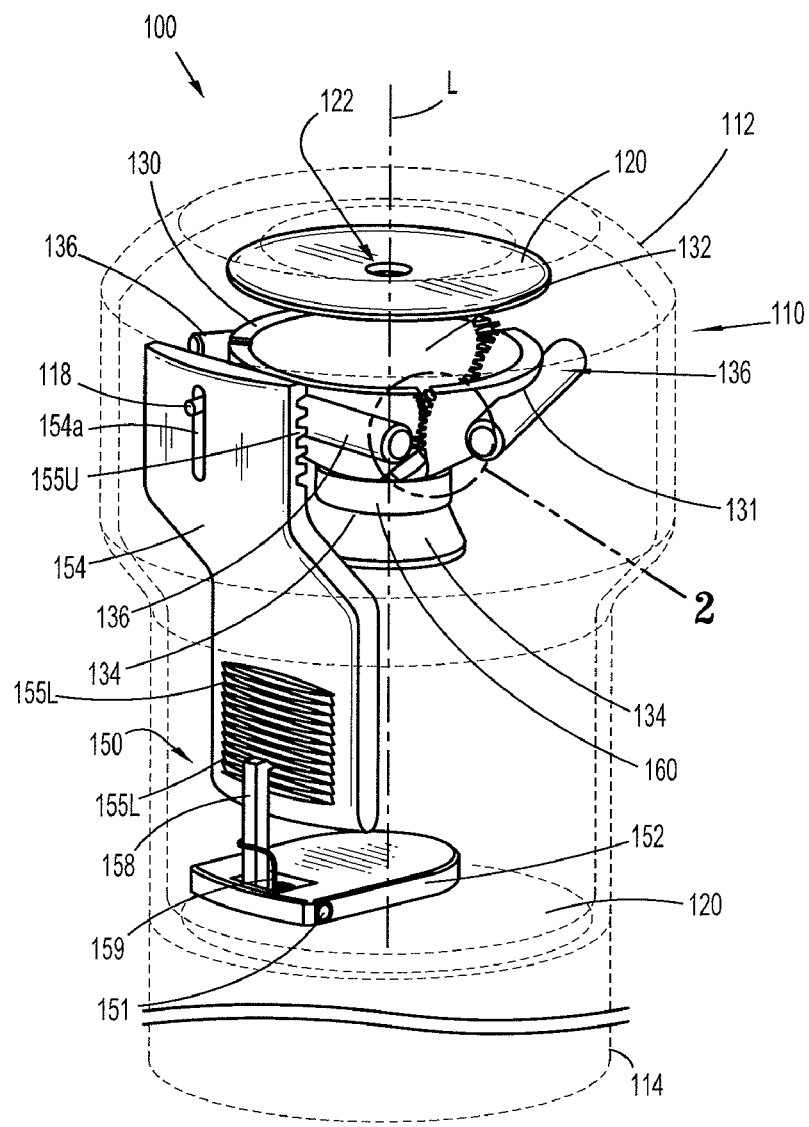
FIG. 1 is a perspective view of a surgical portal apparatus in accordance with the present disclosure.

The surgical portal apparatus of the present disclosure provides a substantial seal between a body cavity of a patient and the outside atmosphere before, during and after insertion and manipulation of an instrument through the seal thereof.

The surgical portal apparatus of the present disclosure contemplates the introduction and manipulation of various types of instrumentation adapted for insertion through a trocar and/or cannula assembly while maintaining a substantially fluid-tight interface about the instrument to preserve the atmospheric integrity of a surgical procedure from leakage. Examples of instrumentation include, but are not limited to, clip appliers, graspers, dissectors, retractors, staplers, laser probes, photographic devices, endoscopes and laparoscopes, tubes, and the like. Furthermore, these instruments can be designed with a variety of tip configurations and a variety of diameters. Such instruments will collectively be referred to as "instruments" or "instrumentation" or "surgical objects." Examples of surgical procedures in which the portal apparatus may be utilized include endoscopic, laparoscopic, and arthroscopic, and other procedures necessitating access to a remote body cavity and potential sealing against the escape of insufflation gases and irrigant fluids.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is farther from the user. In the following description, well-known functions or constructions are not described in detail to avoid obscuring the present disclosure in unnecessary detail.

Referring now to the drawings, in which like reference numerals identify identical or substantially similar parts throughout the several views, FIG. 1 illustrates a surgical portal apparatus 100. In accordance with the present disclosure, the surgical portal apparatus 100 includes a portal 110, one or more seals 120, a plurality of restricting members 130, a gear assembly 140, and a lockout assembly 150.

Referring now to FIGS. 1-5, the portal 110 defines proximal and distal ends 112, 114. Portal 110 is dimensioned for insertion within tissue to access an underlying tissue site (not shown). The portal 110 defines a longitudinal axis "L" and a longitudinal opening 116 for reception of a surgical object "I". One or more seals 120 are disposed in mechanical cooperation with the portal 110. One seal 120 may be mounted proximal of the restricting members 130 and one seal 120 (in phantom in FIG. 1) may be distal of the restricting members 130. The one or more seals 120 may define a passage 122 for reception of the surgical object "I" in substantial sealed relation therewith. Any means for securing the one or more seal 120 are envisioned. One suitable seal is disclosed in commonly assigned U.S. Pat. No. 6,702,787 to Racenet, the entire contents of which disclosed is hereby incorporated by reference herein.

Figure 4:
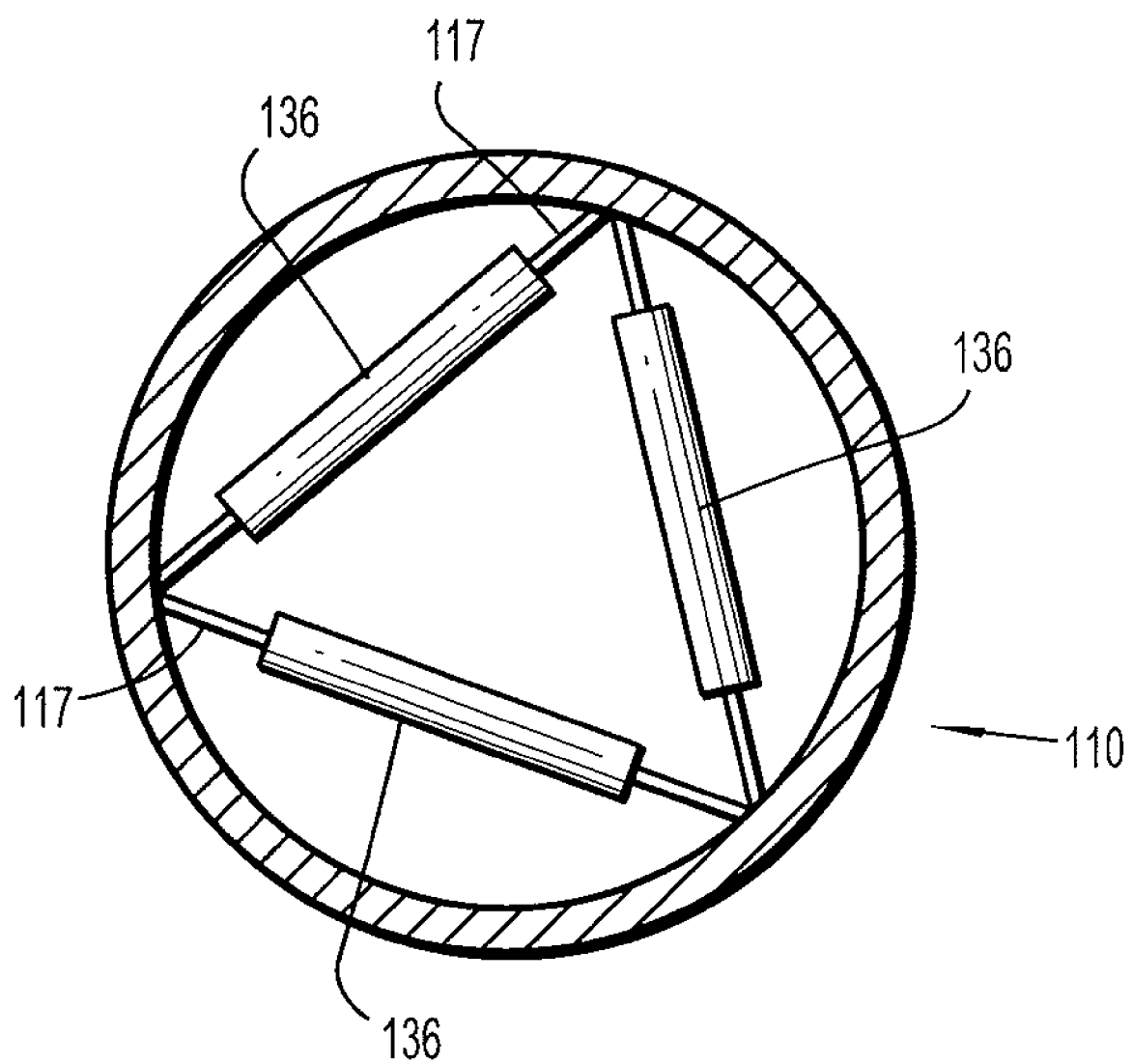
FIG. 4 is a top plan view illustrating the support members for supporting the restricting members.

The plurality of restricting members 130 are arranged about the longitudinal axis "L" to define a passage 132 therethrough and are positioned to contact the surgical object "I" during introduction of the surgical object "I" through the longitudinal opening 116 of the portal 110. The restricting members 130 define a funneled cup when in the initial or at rest position depicted in FIG. 1. The funneled cup arrangement may facilitate guiding of the object "I" through the restricting members 130. Each restricting member 130 is pivotally mounted within the portal 110 via a support segment 136. Each restricting member 130 may pivot, rotate or revolve about a respective support segment 136. As best depicted in FIG. 4, each support segment 136 may be mounted within the portal 110 via mounting pins 117. Mounting pins 117 extend from each support segment 136 and may be secured within the wall of the portal 110. (In FIG. 4, restricting members 130 are shown removed from support segments 136 for clarification purposes). Each support segment 136 may be secured within the portal 110 in a manner whereby the support segment 136 may rotate about the mounting pins 117, or may be mounted in fixed relation to the mounting pins 117. Other mechanisms for mounting support segments 136 within portal 110 are also envisioned including other mechanical fastening systems or with adhesives or the like. In embodiments, each support segment 136 may be substantially cylindrically shaped.

In one embodiment, each restricting member 130 may have an elongated arcuate recess 131 in its outer surface dimensioned for at least partial reception of a respective support segment 136. The elongated arcuate recess 131 may serve as the fulcrum about which each restricting member 130 pivots along a respective support segment 136. For example, each arcuate recess 131 of the corresponding restricting member 130 and each support segment 136 is dimensioned to permit traversing or pivoting movement of one component relative to the other during entry and exit of the surgical object "I".

Each restricting member 130 has a lower or distal contacting segment 134 adapted for radial movement relative to the longitudinal axis "L" from a rest position where the passage 132 defines a first internal dimension to a displaced position where the passage 132 defines a second internal dimension greater than the first internal dimension in response to contact with the surgical object "I."

Figure 2:
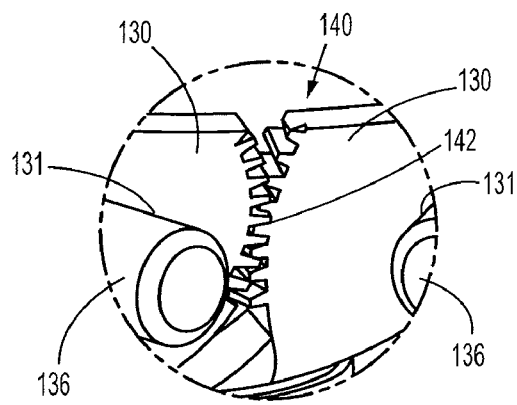
FIG. 2 is an enlarged perspective view of the area of detail 2-2 identified in FIG. 1.
Figure 3:
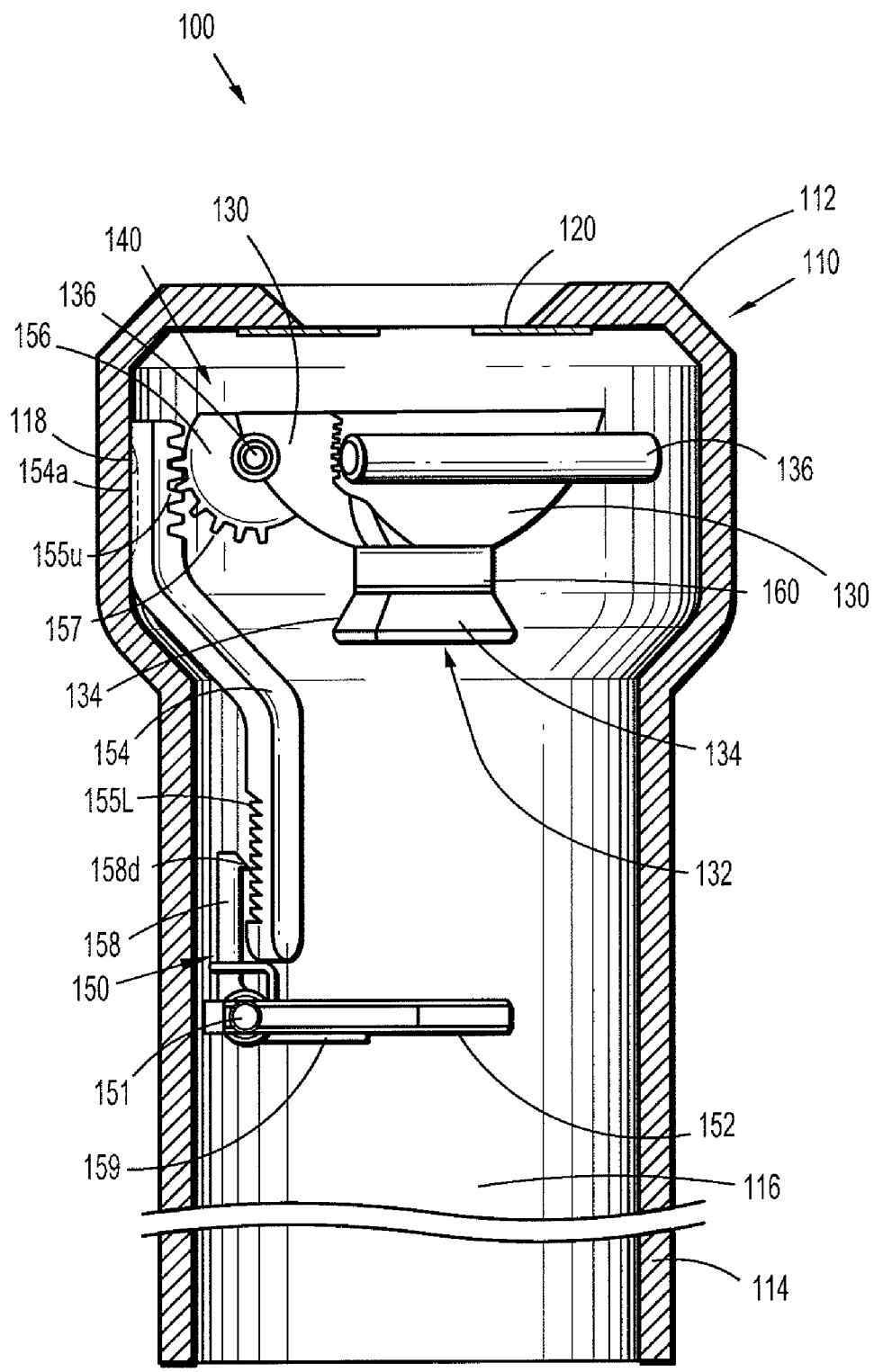
FIG. 3 is a partial cross-sectional view illustrating the restricting members and lockout assembly of the surgical portal apparatus.
Figure 5:
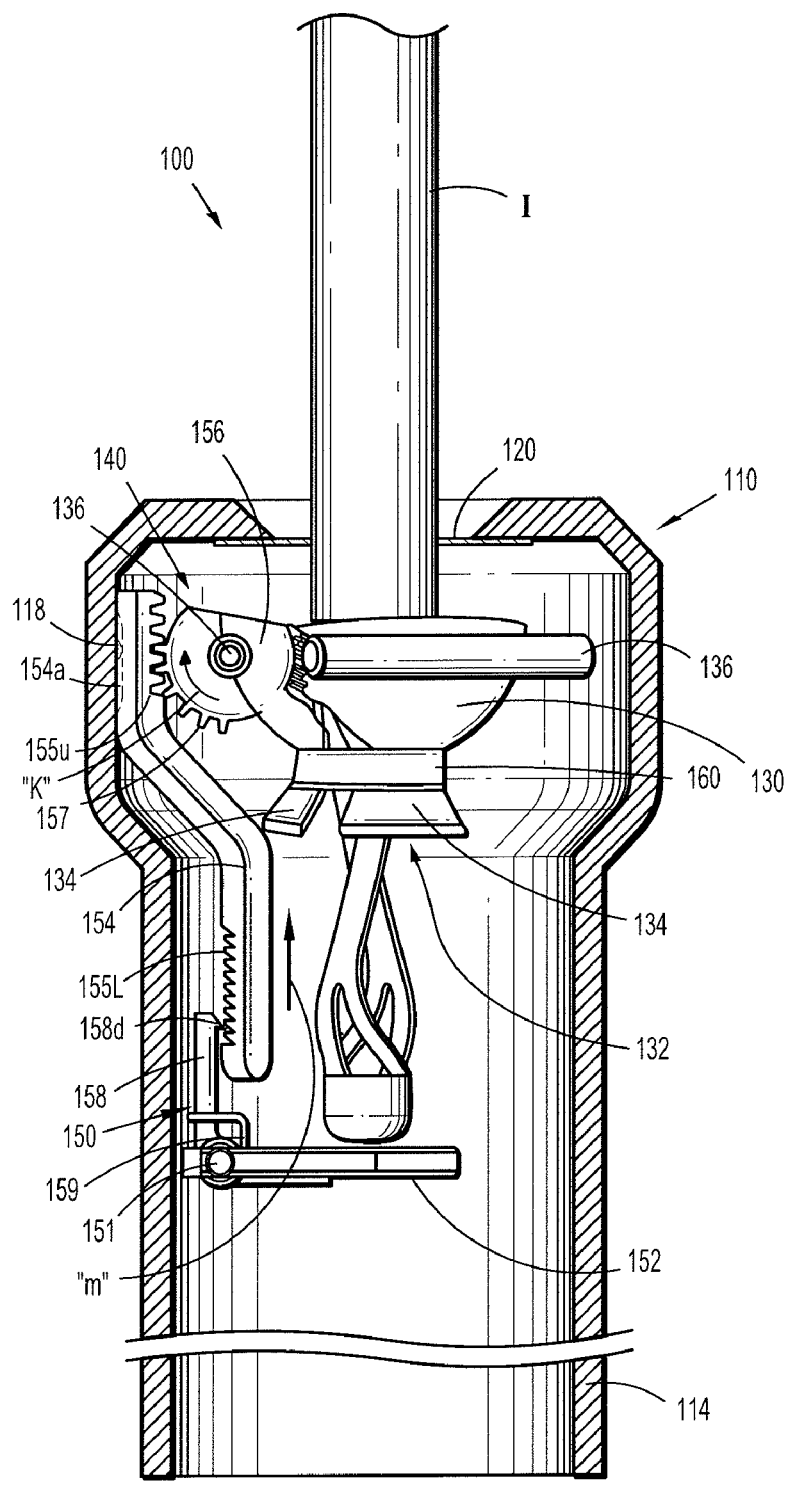
FIG. 5 is a partial cross-sectional view of the surgical portal apparatus illustrating a surgical object introduced through the restricting members.

In addition, each restricting member 130 is operatively coupled whereby the contacting segments 134 of the restricting members 130 concurrently move between the rest position (FIG. 3) and the displaced position (FIG. 5). In one embodiment, a gear assembly 140 is adapted to permit concurrent radial movement of the contacting segments 134 of the restricting members 130 between the rest position and the displaced position. As best depicted in FIG. 2, the gear assembly 140 includes one or more gears 142 which operatively couple with one or more gears 142 of an adjacent restricting member 130. In embodiments, the one or more gears 142 may be spherically beveled and defined at each end segment of the restricting member 130. In embodiments, the one or more gears may have a predetermined radius of curvature. Pivoting movement of one restricting member 130 causes corresponding and simultaneous movement of the adjacent restricting member 130 via the gears 142 between the rest position and the displaced position.

The lockout assembly 150 includes a locking member 152 disposed distal of the restricting members 130. The locking member 152 is positioned to intersect the longitudinal opening 116 and/or passages 132, 122 and engage the surgical object "I" during passage of the surgical object "I" through the longitudinal opening 116 and/or passages 132, 122. The locking member 152 is operatively coupled with the restricting members 130 to substantially prevent radial movement of the contacting segments 134 beyond the displaced position when the surgical object "I" is within the longitudinal opening 116 and/or passages 132, 122 to thereby minimize offset manipulation of the surgical object "I" relative to the longitudinal axis "L." Moreover, the locking member 152 may be adapted to restrict any further pivoting movement of the restricting members 130 when the surgical object "I" is within the longitudinal opening 116 thus minimizing offset manipulation of the object "I" and potentially preserving the integrity of the seal about the object "I" and through the portal apparatus 100.

The lockout assembly 150 includes a rack 154 and associated drive gear 156, (FIGS. 3 and 5) operatively coupled to one of the restricting members 130. The lockout assembly 150 also includes a lock out pawl 158. The rack 154 is mounted to the portal 110 via pin 118. Pin 118 is secured within the internal wall of portal 110 and is received within a slot 154*a* of rack 154 (FIG. 1). The pin 118 is configured to translate the slot 154*a* defined in rack 154 when rack 154 translates in a longitudinal direction. The rack 154 includes upper and lower teeth 155U, 155L. The drive gear 156 may be mounted, secured or integrally formed with an external surface of one of the restricting members 130. The drive gear 156 may be monolithically formed within the restricting member 130. The drive gear 156 rotates about the support segment 136 and includes drive gear teeth 157 which intermesh with upper teeth 155U of rack 154. The drive gear 156 is adapted for rotational movement during rotational movement of the contacting segments 134 between the rest position and the displaced position to cause corresponding longitudinal translation of the rack 154 within the portal 110 via upper and lower teeth 155U, 155L of the rack 154 and drive gear teeth 157.

The lock out pawl 158 is coupled to the locking member 152. The lock out pawl 158 is movable upon movement of the locking member 152 during passage of the surgical object "I" through the longitudinal opening 116 to selectively engage the rack 154 with locking detent 158*d* to secure the rack 154 at a defined longitudinal position corresponding to the displaced position of the contacting segments 134 to thereby substantially prevent radial movement of the contacting segments 134 beyond the displaced position. The locking member 152 is adapted for pivotal movement about pin 151 upon engagement with the surgical object "I" to move the lock out pawl 158 into engagement with the rack 154. Movement of the locking member 152 may cause corresponding and substantially movement of lock out pawl 158 through equal arcs of rotation. In the alternative, the arc rotation of movement of lock out pawl 158 may be different than the locking member 152. This may be achieved with the use of clutch gears, planetary gears systems or any gears producing different ratio of movement, which may be incorporated within one or both of the lock out pawl 158 and the locking member 152. The locking member 152 is normally biased via a biasing spring 159 and a support pin 151 to a position where the lock out pawl 158 is released from the lower teeth 155L of the rack 154 (see FIG. 3). In embodiments, the lock out pawl 158 is configured to ratchetly engage the lower teeth 155L of the rack 154.

The surgical portal apparatus includes a biasing member 160 (e.g., a rubber band) for normally biasing the restricting members 130 toward the first position to urge the surgical object "I" to the general aligned position with the longitudinal axis "L." The biasing member 160 may be made from any flexible material (e.g., elastomeric material) and may be annular in configuration.

In operation, the portal member 110 is introduced within tissue to access underlying tissue site. The restricting members 130 are in the position depicted in FIG. 3. Thereafter, the surgical object "I" is advanced through the portal member 110 as depicted in FIG. 5. During movement, the surgical object "I" is engaged by the lower contacting segments 134 of restricting members 130 which causes the contacting segments 134 to pivot or rotate about their respective support segments 136. As noted, through the interengagement of the restricting member 130 via gears 140, each restricting member 130 pivots in a simultaneous or concurrent manner. Further, as restricting member 130 having gear 156 pivots, the gear 156 rotates in a clockwise direction "k" depicted in FIG. 5 causing the rack 154 to translate in a proximal longitudinal direction depicted by directional arrow "m" through the engagement of the teeth 157 of gear 156 and the teeth 155U of rack 154. Once the full diameter or cross section of the surgical object "I" passes through the restricting member 130, the contacting segments 134 will no longer pivot outwardly in the radial direction. Thus, the degree of pivoting movement of the contacting segments 134 is dependent on the diameter of the surgical object "I" and reaches its maximum displacement when the object is passed through the restricting members 130.

Figure 6:
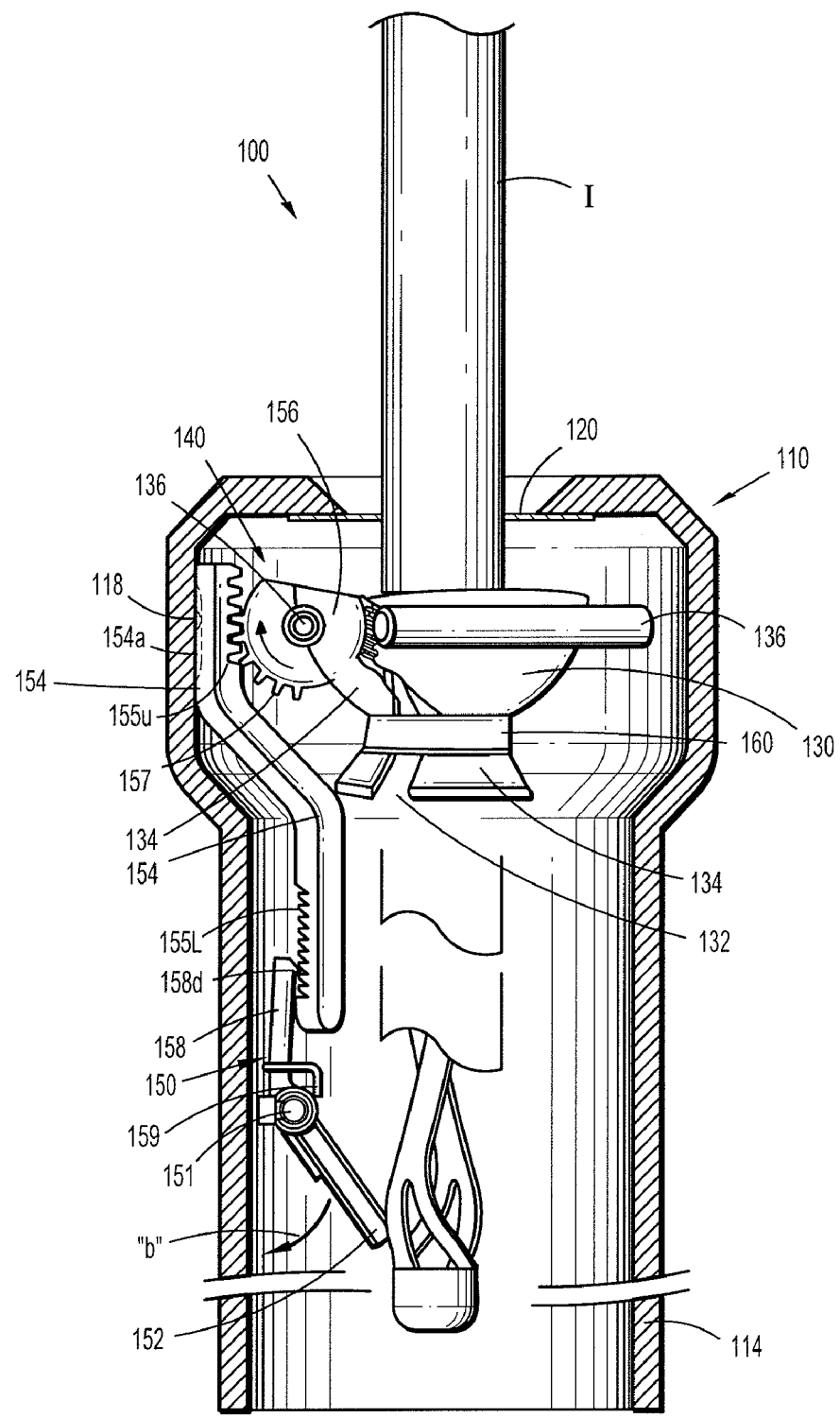
FIG. 6 is a partial cross-sectional view of the surgical portal apparatus illustrating the surgical object engaged with the lockout assembly.

As the surgical object "I" is further advanced, the object engages locking member 152 as depicted in FIG. 6. Locking member 152 pivots in the direction of directional arrow "b" which causes the detent 158*d* of lockout pawl 158 to pivot into engagement with teeth 155L of rack 154. In this manner, rack 154 is restricted from any further movement in a proximal longitudinal direction, which, in effect, prevents any further radial outward movement of contact segments 134 of the restricting members 130 beyond e.g., its maximum displacement. It is noted that in the orientation of the detent 158*d* of pawl 158 and the teeth 155L of rack 154, the rack 154 may translate in a distal longitudinal direction thereby enabling the contacting segments 134 to move in a radial inward direction about the surgical object "I". Surgery is performed, with restricting members 130 in a substantially locked position whereby any excessive offset manipulation of the surgical object "I" is minimized. Elastic band 160 will further bias the contacting segments 134 of the restricting member 130 in a radial inward direction against the surgical object. Once the surgery is completed, the surgical object "I" is removed. Once the object clears the locking member 152, the locking member 152 pivots to the position depicted in FIG. 3 under the influence of spring 159, and locking pawl 158 is displaced from the lower teeth 155L of the rack 154 permitting the restricting members 130 to return to the rest condition of FIG. 3.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical portal apparatus, comprising: a portal defining a longitudinal axis; a plurality of restricting members, each restricting member including a support segment and a contacting segment, the support segment being pivotably secured to the portal to permit radial movement of the contacting segment relative to the longitudinal axis between a rest position and a displaced position; a locking member operatively coupled to one of the restricting members to limit radial movement of the contacting segments beyond the displaced position; a rack and associated drive gear operatively coupled to one of the restricting members, the drive gear adapted for rotational movement during radial movement of the contacting segments between the rest position and the displaced position to cause corresponding longitudinal translation of the rack within the portal; and a lock out pawl coupled to the locking member, the lock out pawl movable upon movement of the locking member to selectively engage the rack to secure the rack at a defined longitudinal position corresponding to the displaced position of the contacting segments.

2. The surgical portal apparatus according to claim 1 wherein the locking member is adapted for pivotal movement upon engagement with the surgical object to move the lock out pawl into engagement with the rack.

3. The surgical portal apparatus according to claim 2 wherein the locking member is normally biased to a position permitting release of the lock out pawl from the rack.

4. A surgical portal apparatus, comprising:
   a portal dimensioned for insertion within tissue to access an underlying tissue site, the portal defining a longitudinal axis and having a longitudinal opening for reception of a surgical object, and defining proximal and distal ends;
   at least one seal disposed in mechanical cooperation with the portal, the at least one seal defining a passage for reception of the surgical object in substantial sealed relation therewith;
   a plurality of restricting members arranged about the longitudinal axis to define a passage therethrough and positioned to contact the surgical object during introduction through the longitudinal opening, the restricting members having contacting segments adapted for radial movement relative to the longitudinal axis from a rest position where the passage defines a first internal dimension to a displaced position where the passage defines a second internal dimension greater than the first internal dimension in response to contact with the surgical object;
   a lockout assembly including a locking member disposed distal of the restricting members, the locking member positioned to intersect the longitudinal opening and engage the surgical object during passage of the surgical object through the longitudinal opening, the locking member operatively coupled with the restricting members to prevent radial movement of the contacting segments beyond the displaced position when the surgical object is within the longitudinal opening, to thereby minimize offset manipulation of the surgical object relative to the longitudinal axis;
   a rack and associated drive gear operatively coupled to one of the restricting members, the drive gear adapted for rotational movement during radial movement of the contacting segments between the rest position and the displaced position to cause corresponding longitudinal translation of the rack within the portal; and
   a lock out pawl coupled to the locking member, the lock out pawl movable upon movement of the locking member during passage of the surgical object through the longitudinal opening to selectively engage the rack to secure the rack at a defined longitudinal position corresponding to the displaced position of the contacting segments, to thereby prevent radial movement of the contacting segments beyond the displaced position.

5. The surgical portal apparatus according to claim 4 further including a biasing member for normally biasing the restricting members toward the rest position to urge the surgical object to a general aligned position with the longitudinal axis.

6. The surgical portal apparatus according to claim 4 wherein the restricting members are operatively coupled whereby the contacting segments of the restricting members concurrently move between the rest position and the displaced position.

7. The surgical portal apparatus according to claim 4 further including a gear assembly for facilitating concurrent radial movement of the contacting segments of the restricting members between the rest position and the displaced position, the gear assembly including at least one gear operatively coupling adjacent restricting members.

8. The surgical portal apparatus according to claim 4 wherein the restricting members are pivotally mounted within the portal, the restricting members being pivotally movable to cause movement of the contacting segments between the rest position and the displaced position.

9. The surgical portal apparatus according to claim 4 wherein the locking member is adapted for pivotal movement upon engagement with the surgical object to move the lock out pawl into engagement with the rack.

10. The surgical portal apparatus according to claim 4 wherein the locking member is normally biased to a position permitting release of the lock out pawl from the rack.

11. A surgical portal apparatus, comprising:
    a portal defining a longitudinal axis;
    a plurality of restricting members, each restricting member including a support segment and a contacting segment, the support segment being pivotably secured to the portal to permit radial movement of the contacting segment relative to the longitudinal axis between a rest position and a displaced position;

a locking member operatively coupled to one of the restricting members to limit radial movement of the contacting segments beyond the displaced position; and a rack and associated drive gear operatively coupled to one of the restricting members, the drive gear adapted for rotational movement during radial movement of the contacting segments between the rest position and the displaced position to cause corresponding longitudinal translation of the rack within the portal.

12. The surgical portal apparatus according to claim 11 wherein the locking member is disposed distally of the restricting members so that the locking member is closer to a leading end of the portal than the restricting members.

13. The surgical portal apparatus according to claim 11 further including a biasing member for normally biasing the restricting members toward the rest position.

14. The surgical portal apparatus according to claim 11 wherein the restricting members are operatively coupled whereby the contacting segments of the restricting members concurrently move between the rest position and the displaced position.

15. The surgical portal apparatus according to claim 11 further including a gear assembly for facilitating concurrent radial movement of the contacting segments of the restricting members between the rest position and the displaced position, the gear assembly including at least one gear operatively coupling adjacent restricting members.

16. The surgical portal apparatus according to claim 11 wherein the locking member is adapted for pivotal movement to move the lock out pawl into engagement with the rack.

17. The surgical portal apparatus according to claim 16 wherein the locking member is normally biased to a position permitting release of the lock out pawl from the rack.

18. The surgical portal apparatus according to claim 11 further comprising at least one seal disposed in mechanical cooperation with the portal.

* * * * *